United States Patent [19]

Chupp et al.

[11] Patent Number: 5,617,860
[45] Date of Patent: Apr. 8, 1997

[54] METHOD AND SYSTEM FOR PRODUCING POLARIZED $^{129}$XE GAS

[75] Inventors: Timothy Chupp; Kevin P. Coulter, both of Ann Arbor, Mich.; Eduardo Oteiza; Ronald Walsworth, both of Cambridge, Mass.

[73] Assignees: Smithsonian Astrophysical Observatory, Cambridge, Mass.; The Regents of the University of Michigan, Ann Arbor, Mich.

[21] Appl. No.: 487,137

[22] Filed: Jun. 7, 1995

[51] Int. Cl.$^6$ ................................................. A61B 5/055
[52] U.S. Cl. ...................... 128/653.4; 128/654; 432/262
[58] Field of Search ..................... 128/653.4, 654, 128/659; 432/262; 204/157.15, 157.2, 157.21, 157.22

[56] References Cited

U.S. PATENT DOCUMENTS

| | | |
|---|---|---|
| 3,996,120 | 12/1976 | Freund et al. . |
| 4,025,790 | 5/1977 | Jetter et al. . |
| 4,029,559 | 6/1977 | Marling . |
| 4,032,306 | 6/1977 | Lee . |
| 4,372,928 | 2/1983 | Chatelet et al. . |
| 4,381,923 | 5/1983 | Wada . |
| 4,386,274 | 5/1983 | Altshuler . |
| 4,505,791 | 3/1985 | Angelie et al. . |
| 4,528,080 | 7/1985 | Donohue et al. . |
| 5,015,348 | 5/1991 | Eerkens . |
| 5,039,500 | 8/1991 | Shino et al. ........................ 423/262 |
| 5,063,746 | 11/1991 | Agrawal et al. . |
| 5,067,976 | 11/1991 | Agrawal et al. . |
| 5,069,698 | 12/1991 | Cheung et al. . |
| 5,110,430 | 5/1992 | Eerkens . |
| 5,122,173 | 6/1992 | Agrawal et al. . |
| 5,186,007 | 2/1993 | Takano et al. . |
| 5,202,005 | 4/1993 | Paisner et al. . |
| 5,316,635 | 5/1994 | Green et al. . |
| 5,357,959 | 10/1994 | Fishman ............................ 128/653.2 |
| 5,545,396 | 8/1996 | Albert et al. . |

OTHER PUBLICATIONS

M.S. Albert et al., Biological Magnetic Resonance Imaging Using Laser–Polarized $^{129}$Xe. *Nature*, vol. 370, Jul. 21, 1994, pp. 199–201.

M.E. Wagshul et al., Optical Pumping Of High–Density Rb With A Broadband Dye Laser And GaAlAs Diode Laser Arrays: Application To $^3$He Polarization. *Physical Review A*. vol. 40, No. 8, Oct. 15, 1989, pp. 4447–4454.

G.D. Cates, et al., Rb–$^{129}$Xe Spin–Exchange Rated Due To Binary And Three–Body Collisions At High Xe Pressures. *Physical Review A*. vol. 45, No. 7, Apr. 1, 1992, pp. 4631–4639.

*Primary Examiner*—Marvin M. Lateef
*Assistant Examiner*—Brian L. Casler
*Attorney, Agent, or Firm*—Harness, Dickey & Pierce, P.L.C.

[57] ABSTRACT

A method and system for producing polarized $^{129}$Xe gas in an economical manner, allowing the polarized $^{129}$Xe gas to be used commercially in research and clinical applications. The production system of the present invention includes a holding tank for holding an unpolarized xenon gas/nitrogen gas mixture. The holding tank is in communication with a temperature controlled polarization chamber. A wide spectrum high power light source such as a diode laser array is in communication with the polarization chamber. The alkali metal vapor is optically pumped by the light source. The polarization chamber, which contains a given quantity of an alkali metal and its associated vapor, receives the gaseous mixture from the holding tank. The optically pumped alkali metal vapor atoms then collide with the xenon gas atoms, thus polarizing the xenon atoms. The entire gaseous mixture expands out of the polarization chamber into a device that separates the alkali metal vapor atoms from the polarized $^{129}$Xe atoms. The polarized $^{129}$Xe atoms are then controllably output to a system/user interface for application purposes.

12 Claims, 5 Drawing Sheets

METHOD AND SYSTEM FOR PRODUCING POLARIZED $^{129}$XE GAS

BACKGROUND OF THE INVENTION

1. Technical Field

This invention relates generally to a gaseous polarization process, and in particular to a method and system for producing polarized $^{129}$Xe gas in a commercially feasible manner.

2. Discussion

Xenon gas, in addition to its present use as a safe general anesthetic, may have a variety of other potential medical applications. When ingested by a subject, xenon is transported from the lungs to the blood and on to the rest of the body, and concentrates in lipid and protein tissues such as those forming the lungs and the brain. Because xenon concentrates in these particular biological environments, the gas nuclear spin ½ isotope, xenon-129 ($^{129}$Xe), when polarized, produces beneficial results when used in magnetic resonance imaging (MRI) applications.

In MRI applications, magnetic resonance signals are produced by weakly polarized proton spins found within biological tissues, with the vast majority of proton spins residing in water molecules. These proton spins are weakly polarized by large magnetic fields: polarizations of approximately $10^{-5}$ in magnetic fields of several tesla are typical. Because the strength of the polarization signal is in direct proportion to the strength of the MRI signal, it is desirable to have a stronger polarization of the protons in the tissues that are being imaged. However, in certain biological environments, such as the lung gas space and lipid membranes in the brain, there is very little water present. Thus, poor quality proton MRI signals are typically produced in these environments.

Highly polarized $^{129}$Xe gas, when inhaled by or injected into a subject and absorbed by biological tissues, creates higher resolution images of these tissues and other weakly polarized MRI environments. Such beneficial results have been experimentally shown as reported by M. S. Albert, G. D. Cates, D. Driehuys, W. Happer, B. Saam, C. S. Springer, Jr., and A. Wishnia in an article entitled "Biological Magnetic Resonance Imaging Using Laser-Polarized $^{129}$Xe", 370 Nature 199 (21 Jul. 1994), hereby incorporated by reference. To date, however, presently-known methods of producing polarized $^{129}$Xe gas have proven to be cost prohibitive from a commercial production standpoint.

Known methods of polarizing xenon gas incorporate a resonant light source to optically pump an alkali metal vapor to transfer the angular momentum of photons from the light source to atoms of the alkali metal vapor via cyclical resonant absorption or scattering. As alkali metal vapor atoms absorb this angular momentum, the non-polarized xenon gas is introduced into the same environment as the optically pumped alkali metal atoms. The optically pumped alkali metal vapor atoms then collide with the non-polarized xenon atoms, thus transferring polarization from the alkali metal vapor atoms to the xenon atoms. These collisions thus polarize certain isotopes including $^{129}$Xe.

Several types of light sources are potentially suitable for optically pumping the alkali vapor. These light sources include: alkali lamps; dye lasers; Ti-sapphire lasers pumped by argon ion lasers; and single mode diode lasers. As discussed below, all of these light sources have significant practical limitations that make them unsuitable for polarizing $^{129}$Xe gas in a commercially viable system.

Lamps are the oldest technology and provide a low power, incoherent light (less than 1 milliwatt) at a modest cost. However, these light sources are not capable of the high power optical pumping required for efficient production of spin polarized $^{129}$Xe gas.

Dye lasers provide a much higher power light than do the aforementioned lamps (up to approximately 1 watt). However, dye lasers are relatively expensive, large, complex, delicate and have high associated maintenance costs. Thus, these lasers are not desirable for the economical production of polarized $^{129}$Xe gas.

Ti-sapphire laser systems are desirable for optical pumping as they can provide up to 5 watts of narrow spectrum light with a spectral width of less than 30 GHz. However, Ti-sapphire laser systems suffer similar impracticalities associated with dye lasers: the laser systems are delicate, large in size, have associated high maintenance costs and are expensive (approximately $100,000 for a complete Ti-sapphire laser system).

Single mode diode lasers are desirable for optical pumping as they are small, robust and relatively inexpensive. However, these lasers provide less than 200 milliwatts of narrow spectrum light (i.e., a spectral width of less than 10 GHz). Because of their low power, single mode diode lasers can not efficiently polarize large quantities of $^{129}$Xe gas.

Another commercially available light source is the diode laser array. Diode laser arrays are desirable because they are small in size, robust, portable, easy to operate and maintain, and have relatively inexpensive initial cost (approximately $10,000 for a complete laser system). Typical diode laser arrays can provide tens of watts of power over a spectral width of about 1000 GHz at the alkali vapor optical pumping transition, and are solid state devices. Diode laser arrays to date have not been thought to be practical for optically pumping an alkali metal vapor in a $^{129}$Xe polarization process because of their large spectral width.

Diode laser arrays have been used to polarize $^3$He, as isotope of helium, as set forth by M. E. Wagshul and T. E. Chupp, in an article entitled "Optical Pumping Of High Density Rb With A Broadband Dye Laser And GaAlAs Diode Laser Arrays: Application To $^3$He Polarization," 40 Physical Review 4447 (1989) which is hereby incorporated by reference. However, the process of polarizing $^3$He and $^{129}$Xe gases differ significantly due to the different elemental properties associated with each gas, including atomic masses (the ratio of the atomic mass of helium versus the atomic mass of xenon is approximately 1:43), atomic size, nuclear size and atomic chemistry. These differences are manifested in quantitive and qualitative differences. For instance, the rate of alkali to $^{129}$Xe polarization transfer is hundreds of times larger than the rate of alkali to $^3$He polarization transfer. Also, alkali-$^{129}$Xe van der Waals molecules can form in a polarization chamber, but alkali-$^3$He molecules cannot. Further, special materials (e.g. aluminosilicate glass) or special treatments must be used to construct a $^3$He polarization chamber because the very small $^3$He atom can diffuse into the walls of many common materials (e.g. Pyrex glass) and quickly be de-polarized. The much larger $^{129}$Xe atom does not have this diffusion problem. In addition, because $^{129}$Xe is much more chemically active than $^3$He, a $^{129}$Xe polarization chamber's inner walls must generally be coated with a special material (e.g. octadecyltrichlorosilane) to prevent de-polarization. No special coating is needed for $_3$He. Finally, the polarization of the $^3$He and $^{129}$Xe gas require significantly different operating temperatures, alkali vapor pressures, different polarization chamber construction materials and different optical intensities. Because of these differences, commercially available diode laser arrays have not been recognized as a viable alternative for a xenon gas polarization system. Nevertheless, as discussed below, it has been discovered that diode laser arrays are effective in polarizing $^{129}$Xe gas by optically pumping an alkali metal vapor.

Therefore, what is needed is a polarization system incorporating a high power light source such as a diode laser array that is small, robust, and relatively inexpensive, to optically pump an alkali metal vapor to produce polarized $^{129}$Xe gas in a cost-effective and heretofore unachieved manner.

SUMMARY OF THE INVENTION

Accordingly, the present invention provides a system for producing polarized $^{129}$Xe gas that is small enough in size to be implemented easily in a clinical environment. The system of the present invention is also relatively simple in construction, therefore simplifying operation of the system and thus minimizing the need for highly skilled technical personnel. Further, because the system of the present invention utilizes a laser diode array as the light source for optical pumping in the system, system cost is relatively inexpensive when compared to presently available systems. Because of the above characteristics, the system of the present invention allows $^{129}$Xe gas to be produced in a commercially feasible manner, therefore allowing the $^{129}$Xe gas to be used in a wide variety of medically-related clinical and research applications.

According to a preferred embodiment of the present invention, a system is provided for producing polarized $^{129}$Xe gas that includes a storage tank containing a mixture of non-polarized xenon gas along with a buffer gas. The system also includes a polarization chamber for controllably receiving a quantity of the xenon gas/buffer gas mixture from the storage tank. The polarization chamber contains a predetermined quantity of an alkali metal having an associated alkali metal vapor. A wide spectrum, high power light source is positioned relative to the polarization chamber. This light source, which is preferably a laser diode array, optically pumps the alkali metal vapor, causing collisional polarization of the xenon gas present in the polarization chamber with the optically pumped alkali metal vapor atoms. The system also includes means for separating the alkali metal vapor from the polarized xenon gas subsequent to the polarization of the xenon gas.

The system also includes a temperature control chamber housing the polarization chamber, for regulating the pressure, and therefore the density, of the alkali metal vapor to thereby cause efficient collisional polarization of the non-polarized xenon gas. Further, the polarization chamber may include a coating on its interior walls for preventing depolarization of the polarization $^{129}$Xe gas as the polarized gas collides with the chamber walls. In addition, the light of a wide spectrum, high power light source is projected along a direction of a magnetic field associated with the system. This magnetic field may be produced by a magnetic resonance imaging machine. The light from the high power light source is projected through the polarization chamber and is resonant with an alkali atomic transition that induces an electron spin polarization in the alkali metal vapor collinear to the magnetic field via the optical pumping process.

These and other various advantages and features of the present invention will become apparent from the following description and claims, in conjunction with the appended drawings:

BRIEF DESCRIPTION OF THE DRAWINGS

FIG. 6 is a flow diagram illustrating a preferred method in which the system of the present invention polarizes the xenon gas.

DETAILED DESCRIPTION OF THE PREFERRED EMBODIMENTS

Figure 1:
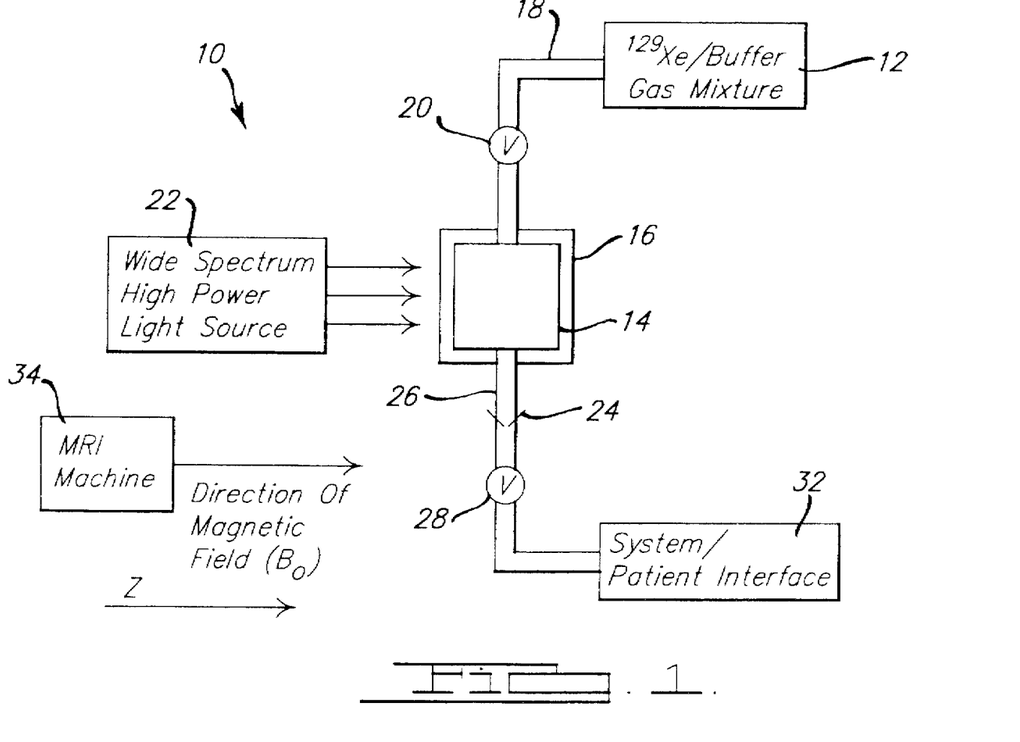
FIG. 1 is a block diagram of a xenon polarization system according to a preferred embodiment of the present invention.

Referring now to FIG. 1 of the drawings, a system for producing polarized $^{129}$Xe gas is shown generally at 10. The system includes a storage tank 12 for holding a gaseous mixture of unpolarized xenon gas and a buffer gas such as nitrogen. The system also includes a polarization chamber 14 housed within a temperature controlled chamber 16. The polarization chamber 14 is connected to the storage tank 12 through tubing 18 and an input valve 20. The system further includes a wide spectrum high power light source 22 that is in direct communication with the polarization chamber 14 in a manner set forth in detail below. Also, an alkali metal vapor separator 24 is in communication with the polarization chamber 14 through tubing 26. Below the alkali metal vapor separator 24 is an output valve 28 for controlling the supply of polarized $^{129}$Xe gas to a user through a system/user interface 32. In a preferred embodiment, the system 10 is implemented in conjunction with an existing commercially available MRI machine 34.

The storage tank 12 is of the type well-known in the art and holds the xenon/nitrogen gas mixture in a gaseous state for use in the polarization chamber 14. The xenon in this gas mixture includes a certain concentration of the $^{129}$Xe isotope. Typically, the $^{129}$Xe isotope comprises 20%–80% of the xenon gas. However, the percentage of the $^{129}$Xe isotope present in the xenon gas may vary. The xenon/nitrogen gas mixture is selectively supplied to the polarization chamber 14 through tubing 18 and the input valve 20, both of which are of a type well-known in the art. The input valve 20 preferably is an automatic valve of the type that may be remotely operated through computer-implemented controls. However, the input valve 20 may also be a manually-operated input valve.

Figure 2:
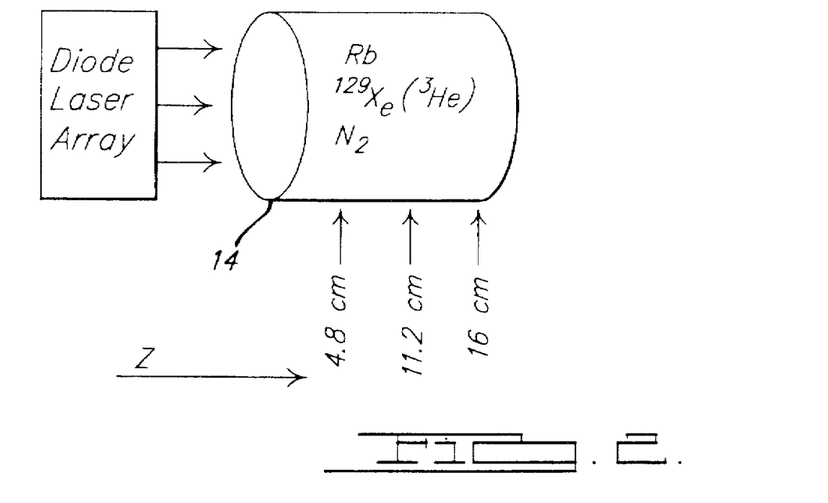
FIG. 2 is a view of a diode laser array implemented with the polarization chamber shown in FIG. 1.

The polarization chamber 14 is preferably composed of an appropriate material such as glass that allows light from the wide spectrum high power light source 22 to pass through the chamber to react with the gaseous mixture inside as will be described in more detail below. The polarization chamber 14 includes a predetermined amount of alkali metal and its associated alkali metal vapor input into the chamber 14 either manually or through an automatic supply mechanism (not shown). As shown in FIG. 2, a polarization chamber according to one embodiment of the present invention is cylindrical and has a length of 16 cm in the Z direction as indicated and a width of 2 cm. However, it should be understood that polarization chamber dimensions may vary according to a particular application. Also, the chamber 14 may be treated on its inner surface with an appropriate coating, such as octadecyltrichlorosilane (OTS), to minimize loss of polarization of the polarized $^{129}Xe$ atoms due to collisions between the atoms and the chamber walls. The polarization chamber allows passage of light from the wide spectrum high power light source 22 at wavelengths appropriate for optical pumping of the alkali metal vapor.

The polarization chamber 14 is housed within the temperature control chamber 16. The temperature control chamber 16 maintains the alkali metal vapor at a density appropriate for optimum collisional polarization of the xenon gas. The control chamber 16 includes temperature sensors (not shown) for monitoring the temperature of the polarization chamber 14. These temperature sensors are in turn connected to control circuitry (not shown) and a processor (not shown) of the type well-known to those skilled in the art for electronic monitoring and control of the temperature to insure that predetermined polarization chamber parameters are met.

The wide spectrum, high power light source 22 is placed in position to optically pump the metal vapor atoms present in the polarization chamber. In the preferred embodiment of the present invention, this light source is a commercially available tunable broadband light source such as a diode laser array of the type well known to those skilled in the art. However, it is contemplated that any semiconductor laser array exhibiting characteristics similar to the diode laser array may be implemented for optical pumping. It should be understood that such a tunable broadband light source typically has a spectral width that is tens of times greater than the absorption width of the alkali metal vapor that is optically pumped.

The light output from the light source 22 is collimated and circularly polarized or separated into two collimated beams with perpendicular linear polarizations which are separately circularly polarized. The light is also resonant with an alkali atomic transition that induces an electron spin polarization in the alkali vapor atoms that is collinear to $B_0$, the direction of the magnetic field induced by the MRI system 34. It should be noted that $B_0$, the direction of the magnetic field, is parallel to the Z axis in FIG. 2. In the preferred embodiment of the present invention, rubidium is the alkali metal vapor present in the polarization chamber. Thus, the diode laser array utilized in the preferred embodiment of the present invention is constructed to output light having a center frequency of 795 nm, the resonant frequency of the rubidium D1 transition.

The alkali metal vapor separator 24 separates the alkali metal vapor/$^{129}Xe$/buffer gas mixture subsequent to polarization of the $^{129}Xe$ gas, allowing the $^{129}Xe$ gas and the buffer gas to pass down through to the output valve 28 and on to the system/user interface 32. The separator, which may be composed of teflon, separates the gaseous mixture by allowing the $^{129}Xe$ gas and buffer gas to pass while retaining the alkali metal vapor.

The tubing 26 and the output valve 28 are similar in function and structure to the tubing 18 and the input valve 20.

The system/user interface 32 may be one of several types. The interface may be a storage tank such as the storage tank 12 for storing the polarized $^{129}Xe$ gas. Due to the relatively short spin polarization lifetime of $^{129}Xe$, however, the interface 32 is preferably of the type that allows direct application of the gas to the end user. Particularly, in a preferred embodiment of the present invention, the interface is a ventilator or other type of applicator allowing ingestion of the $^{129}Xe$ gas directly into the user for purposes described above and set forth in more detail below.

As discussed previously, a diode laser array has proven to be effective in the optical pumping of $^3He$, as set forth by M. E. Wagshul and T. E. Chupp in the article entitled "Optical Pumping Of High Density Rb With A Broadband Dye Laser And GaAlAs Diode Laser Arrays: Application To $^3He$ Polarization," 40 Physical Review 4447 (1989), which has been incorporated by reference. Similar results have not been shown for the use of a diode laser array for optical pumping of xenon due in part to reasons graphically set forth below.

Figure 3A:
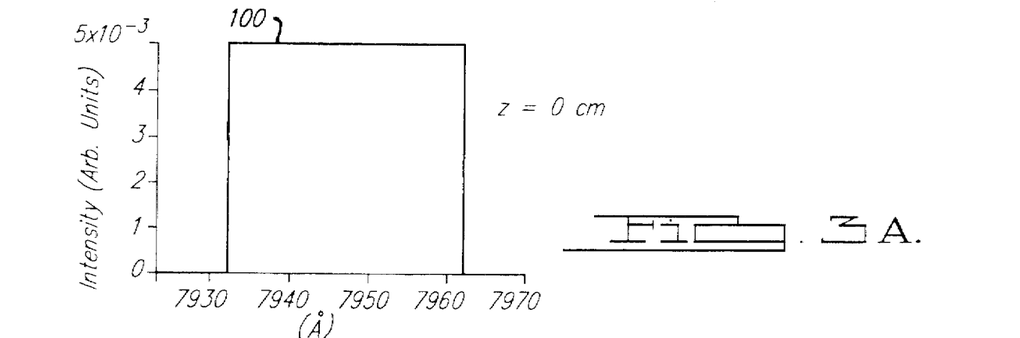
FIGS. 3a–3d are graphical representations of the calculated absorption of laser light by alkali vapor atoms in the polarization chamber shown in FIG. 2.
Figure 3B:
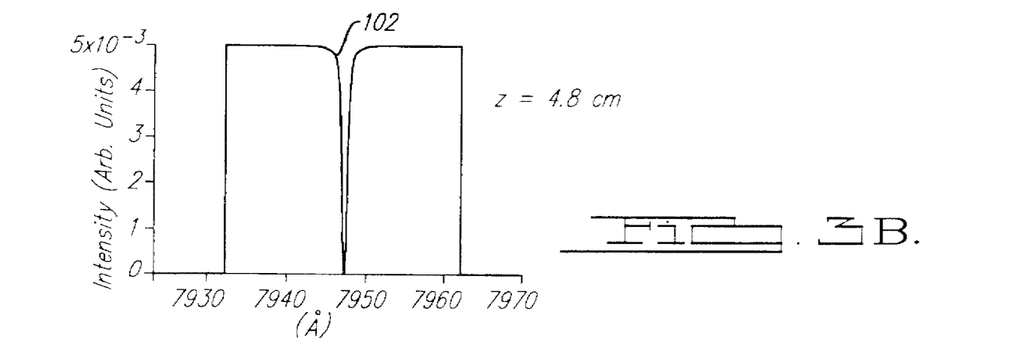
Figure 3C:
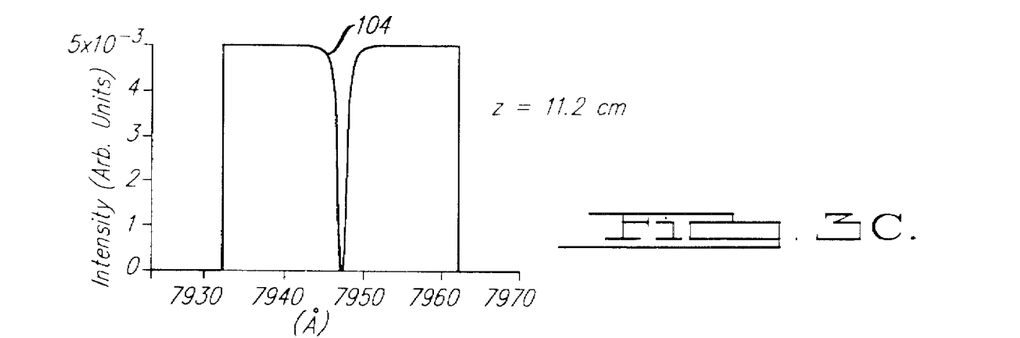
Figure 3D:
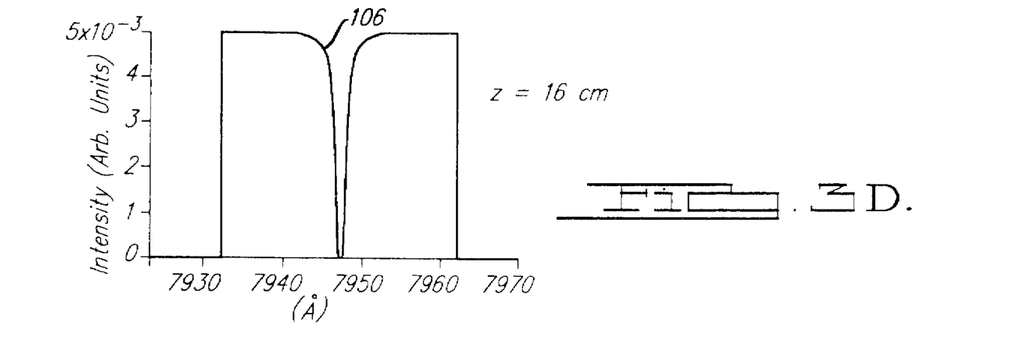
Figure 4A:
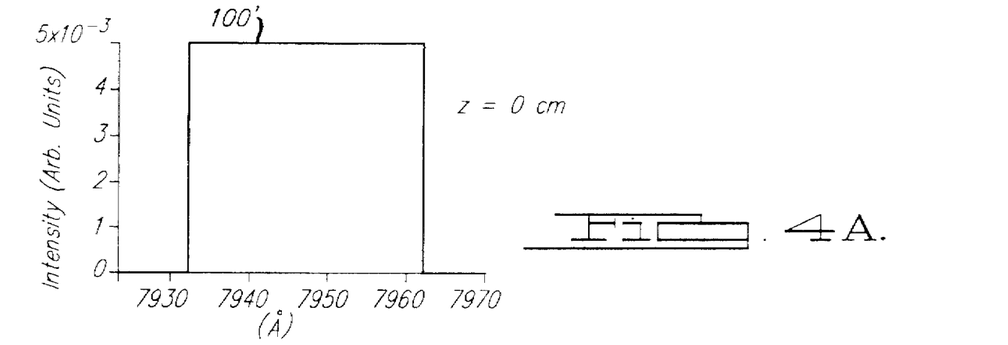
FIGS. 4a–4d are graphical representations of the calculated absorption of light by alkali vapor atoms in a helium optical pumping system.

Referring now to FIGS. 2, 3a-3d and 4a-4d, the calculated absorption of laser light by rubidium atoms in $^{129}Xe$ and $^3He$ optical pumping systems, respectively, are graphically represented. As shown in FIGS. 3a and 4a, lines 100 and 100' represent the even distribution of light from a broadband source such as the diode laser array shown in FIG. 2 over a spectral width of 1.5 nm on either side of 795 nm, the resonant frequency of rubidium. This distribution of light is plotted versus the intensity of the light.

Figure 4B:
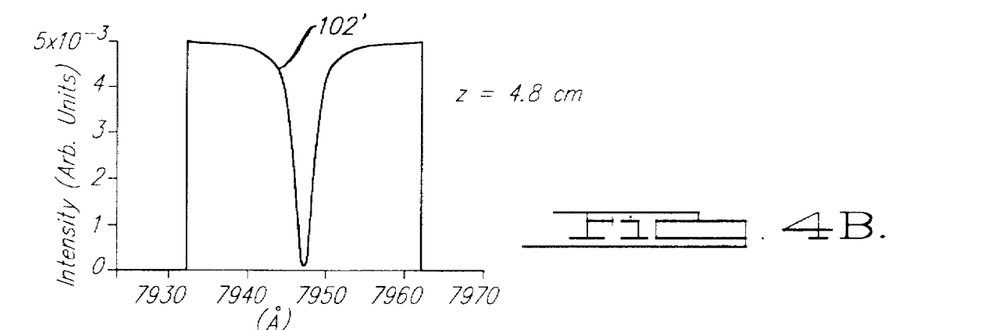
Figure 4C:
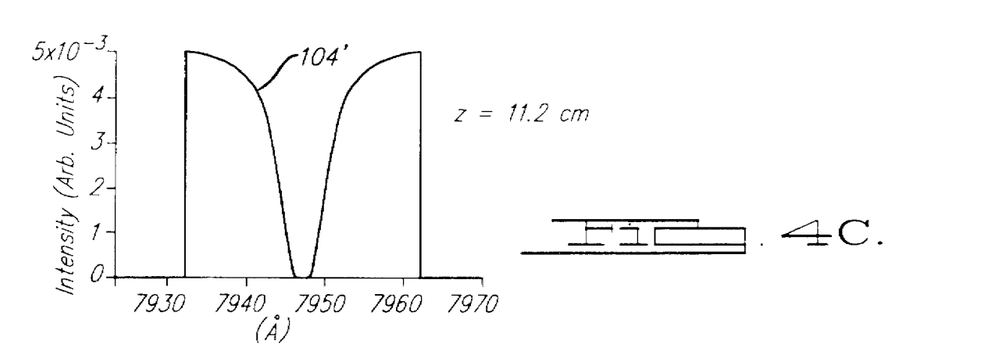
Figure 4D:
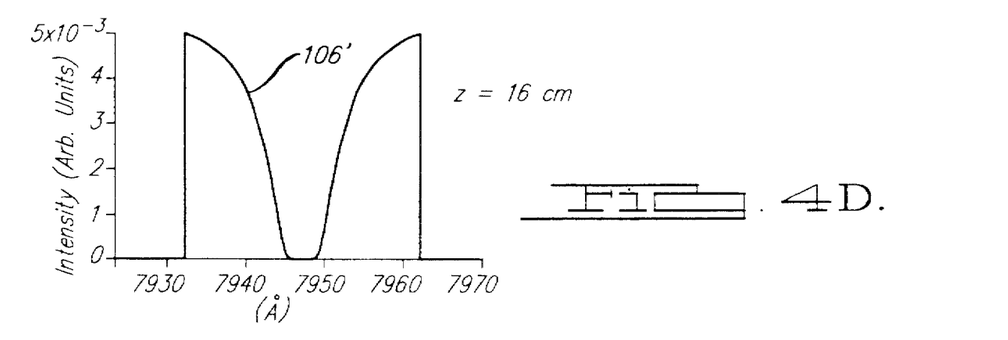

As shown in FIGS. 2, 3b and 4b, as the light penetrates the polarization chamber 14 to a depth of approximately 4.8 cm, the rubidium absorbs the photons from the diode array as indicated at 102 and 102'. As shown in FIGS. 3c and 4c, and as indicated at 104 and 104', photons are absorbed over a wider spectral width as the light penetrates to 11.2 cm into the polarization chamber in the $^3He$ system. Similarly, as shown in FIGS. 3d and 4d, and as indicated at 106 and 106', the rubidium absorbs photons over an even greater spectral width as the light penetrates to 16 cm into the chamber, as off resonant photons are absorbed as well. The spectral width of absorption shown in FIGS. 3b–3d is more narrow than that shown in FIGS. 4b–4d due to the lower rubidium density chosen to compensate for rubidium-xenon depolarization collisions that depolarize the light absorbing rubidium atoms. For practical purposes, the spectral width of absorption in FIGS. 4b–4d is not effectively limited by rubidium-helium collisions, as the collisions are 6000 times weaker, particularly when compared to the xenon-rubidium collisions. As such, more helium may be introduced into the polarization chamber during the pumping process which broadens the rubidium absorption, thus rendering more efficient the absorption of light further from resonance and utilizing a much greater portion of the available spectrum of broadband light.

In view of the above graphical data, it would initially appear that a diode laser array is more suited to optical pumping of $^3He$ than of $^{129}Xe$. However, a diode laser array is highly effective for optical pumping of $^{129}Xe$ for reasons set forth in the description of the polarization chamber operation given below.

Operation of the polarization chamber 14 will now be particularly described. Initially, a predetermined quantity of alkali metal is supplied to the chamber, and the associated alkali metal vapor within the chamber is optically pumped by the light source 22. Referring to the preferred embodiment of the present invention, to optically pump rubidium, the D1 transition may be used from the $5\,s_{1/2}$ ground electric state to the $5\,p_{1/2}$ excited state, with a light wavelength of approximately 795 nanometers.

It should be understood at this point that the term optical pumping is used to describe the transfer of angular momentum from photons to atoms by a cyclical resonant absorption or scattering that occurs to the alkali metal vapor atoms present in the polarization chamber when the light source 22 is energized. For collimated optical pumping light that is right circularly polarized, conservation of angular momentum requires the absorption of a photon to increase the angular momentum of the alkali metal vapor atoms collinear with the light path. For collimated optical pumping light that is left circularly polarized, conservation of angular momentum requires the absorption of a photon to decrease the component of an alkali metal vapor atoms angular momentum collinear with the light path. Thus, for an alkali atomic transition appropriate for optical pumping (e.g., the rubidium D1 transition) the conservation law is expressed as as $\Delta M_s = \pm 1$, where $\Delta M_s$ is the radiation induced change in the alkali atom electron spin orientation quantum number $M_s$, and the conditions +1 and −1 refer to right and left circularly polarized light, respectively.

The dense xenon and buffer gases in the polarization chamber 14 induce rapid collisional de-excitation of optically excited alkali vapor atoms, with equal probability to all electron spin orientations ($M_s$ states) in the ground electronic state, through depopulation optical pumping. This collisional de-excitation prevents radiation trapping, the multiple scattering of unpolarized fluorescent light by the alkali vapor which can reduce the polarization of the alkali vapor and hence polarization of the $^{129}$Xe gas. For an appropriate electronic transition, such as the Rb D1 transition, alkali vapor atoms that inhabit or are collisionally de-excited into the $M_s=+\frac{1}{2}$ state for right circularly-polarized light, or the $M_s=-\frac{1}{2}$ state for left circularly-polarized light, can no longer be excited by the optical pumping light because the angular momentum conservation condition $\Delta M_s=\pm 1$ cannot be satisfied. Atoms in such a "dark" $M_s$ state remain in that state. Eventually most of the alkali vapor atoms collect in the dark $M_s$ state and the ensemble is polarized. (For typical system parameters equilibrium alkali vapor polarization is reached in a few microseconds.)

Collisions in the polarization chamber between the polarized alkali vapor atoms and the xenon gas atoms transfer polarization (i.e. angular momentum) from the spin ½ alkali atom valence electrons to the spin ½ xenon nuclei. The angular momentum transfer occurs because of the transient hyperfine interaction that exists between the alkali atom valence electron and the $^{129}$Xe nucleus during an alkali-xenon atomic collision. For appropriate system parameters and sufficient optical pumping light, the time for an alkali vapor atom to be polarized via optical pumping is much smaller than the time for an alkali vapor atom's polarization to be transferred to a $^{129}$Xe gas atom. Thus, after a collisional transfer of polarization to a $^{129}$Xe gas atom, an alkali vapor atom will be repolarized effectively instantaneously, ready to transfer polarization to another $^{129}$Xe atom. For typical system parameters, the time to reach equilibrium $^{129}$Xe polarization is about ten minutes. The typical equilibrium $^{129}$Xe polarization is 25–75%.

There are two mechanisms whereby $^{129}$Xe nuclei are polarized by the optically pumped alkali metal vapor: i) binary collisions, and ii) the formation of loosely bound van der Waals molecules (in contrast to $^3$He for which only binary collisions contribute). Binary collisions between $^{129}$Xe and alkali vapor atoms have an interaction time on the order of $10^{-12}$ seconds. During this brief interval the alkali valence electron cloud significantly overlaps the $^{129}$Xe atom electron cloud, which in turn overlaps the $^{129}$Xe nucleus. Quantum indistinguishability of electrons, however, allows the alkali valence electron to spend part of its time overlapping the $^{129}$Xe nucleus as well. Thus, there is a contact dipole-dipole (i.e., hyperfine) interaction between the alkali electron and the $^{129}$Xe nucleus during the collision.

This transient hyperfine interaction is greatly enhanced for a large nucleus such as that of $^{129}$Xe (54 protons and 75 neutrons) as compared to a small nucleus such as that of $^3$He (2 protons and 1 neutron) for two reasons: (i) there is a much greater overlap of the atomic electrons (and hence the alkali valence electron) with a large volume $^{129}$Xe nucleus as compared to a small volume $^3$He nucleus; and (ii) the atomic electrons (and hence the alkali valence electron) are pulled closer to a large nucleus because the positive nuclear charge is less well shielded by the negative electron charges for a larger volume nucleus. Using rubidium (Rb) as the alkali polarization transfer medium, the rate constant for Rb to $^{129}$Xe polarization transfer is about 2,000 times larger than the rate constant for Rb to $^3$He polarization transfer.

An alkali $^{129}$Xe van der Waals molecule can be formed in a three-body collision between an alkali vapor atom, a xenon atom, and a third body (typically another $^{129}$Xe atom or a buffer gas molecule). The third body must remove sufficient energy from the alkali-$^{129}$Xe pair to leave them bound in a van der Waals molecule. Also the interaction potential between the alkali and $^{129}$Xe atom must support such a bound state. For example, rubidium and $^{129}$Xe form van der Waals molecules near room temperature, whereas rubidium and $^3$He do not because of their very weak interaction.

Once bound in a van der Waals molecule, the hyperfine interaction time between the alkali atom valence electron and the $^{129}$Xe nucleus can be greatly increased over the typical interaction time of a binary collision. However, at low total gas pressures in the polarization chamber the rate of three body collisions necessary to form van der Waals molecules is very small, whereas at high gas pressures the lifetime of the van der Waals molecules is very short because of destructive collisions with other atoms. In the preferred embodiment of the present invention, for typical system parameters, both the binary collision and van der Waals molecule mechanisms for polarization of $^{129}$Xe are important.

A very-wide-spectrum, high power light source such as a diode laser array is ideal for the polarization of the alkali vapor, and hence the $^{129}$Xe gas, for three reasons: (i) the nitrogen buffer gas density can be made large, thus broadening the Rb absorption line, and the very wide spectrum of the light source interacts strongly with the full pressure-broadened atomic line of the alkali vapor; (ii) the very wide spectrum of the light source can interact strongly with alkali atoms several atomic linewidths off resonance because the alkali vapor in the polarization chamber can be made optically thick; and (iii) very-wide-spectrum, high power light sources such as diode laser arrays are typically smaller, more efficient, much less expensive, and more robust than the alternative narrow-spectrum, high power light sources such as a Ti-sapphire laser. For typical system parameters, the linewidth of the alkali vapor optical pumping transition is pressure broadened to a few tens of GHz by the presence of dense $^{129}$Xe and buffer gases.

Figure 5:
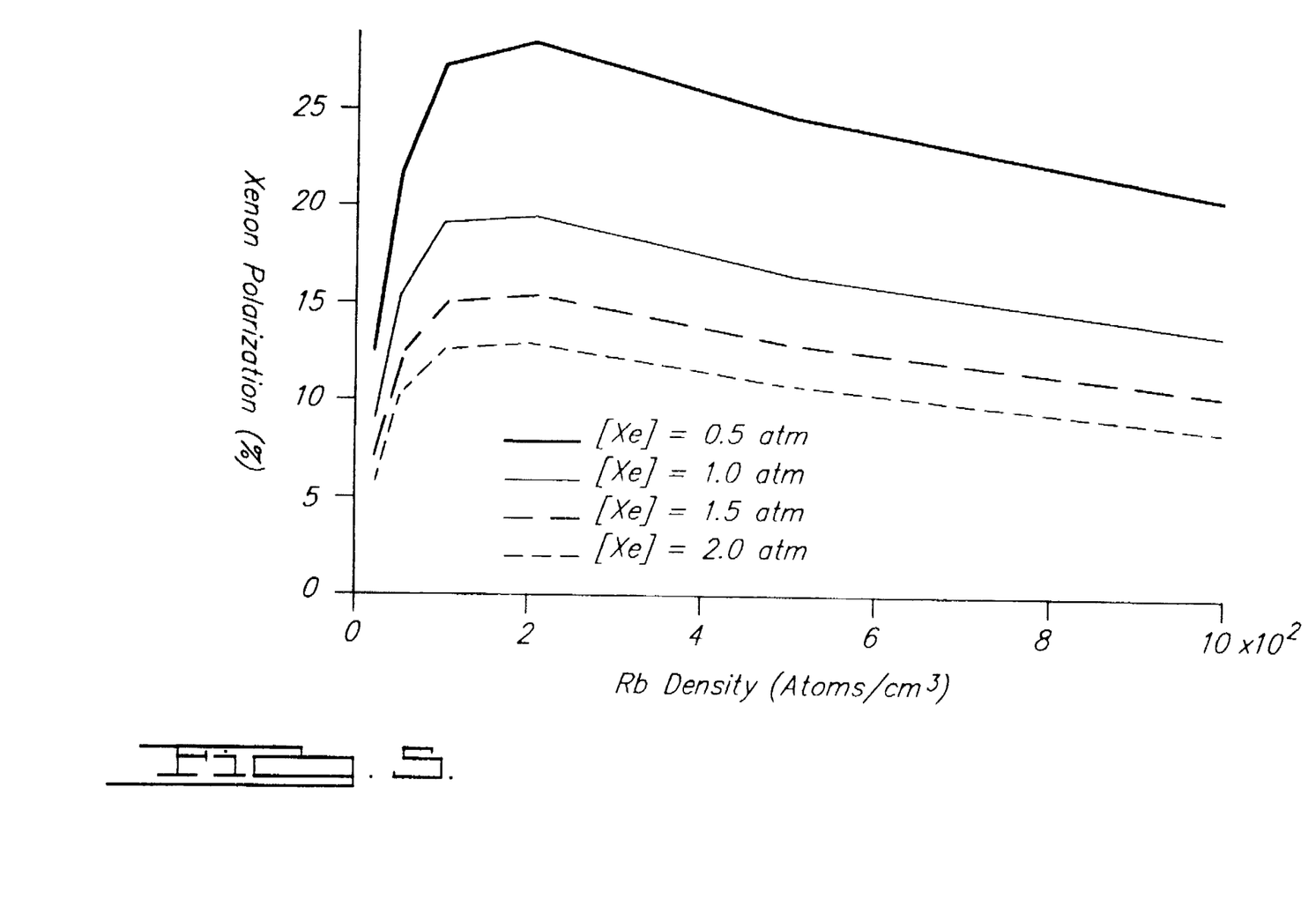
FIG. 5 is a graph of rubidium density versus calculated xenon polarization for xenon at varying atmospheric pressures.

FIG. 5 is a graphical analysis of rubidium density, plotted along the X axis, versus xenon polarization percentage, plotted along the Y axis, for $^{129}$Xe atoms present in a polarization chamber with parameters indicated in Table 1 below at varying $^{129}$Xe pressures, and with a nitrogen buffer gas at a fixed pressure. It is assumed that the diode laser array optically pumping the rubidium atoms is tuned to 795 nm, the resonant frequency of the rubidium D1 transition. As can be seen, the polarization of optically pumped $^{129}$Xe has an optimum value of rubidium density and generally decreases as xenon pressure increases. This decrease is due to the rubidium-$^{129}$Xe collisions taking place within the chamber and due to the fact that the relative number of $^{129}$Xe atoms increases. Thus, maximum polarization of the $^{129}$Xe depends directly on xenon pressure and rubidium density. These variables must be taken into consideration during system setup and during the polarization process.

For off-resonant light, the photon-atom interaction falls off following a roughly Lorentzian pressure-broadened alkali atom lineshape. Thus, for light several linewidths off the atomic resonance, the interaction with the alkali vapor is less than that of light at the resonance frequency. Nevertheless, for typical system parameters, such as those given below in Table 1, resonant optical pumping photons are absorbed in the front of the polarization chamber, while far-off-resonance photons, which penetrate more deeply into the chamber, are also very effective for optical pumping. Since both photon types are absorbed, both contribute to the average alkali metal vapor polarization throughout the chamber. Therefore very-wide-spectrum light sources are able to interact strongly with the alkali vapor over a much wider spectral range than narrow-spectrum light sources, and are effective at optically pumping the alkali vapor and polarizing the $^{129}$Xe gas.

TABLE 1

| | |
|---|---|
| Rb Density | 2e12/cc |
| Xe Density | 1.5e19/cc to 6e19/cc |
| Nitrogen Density | 7e18/cc |
| Polarization Chamber Parameters | 32 cm length, 100 cc volume per 20 W laser diode array |
| Polarization Chamber Temperature | 85° C. |
| Diode Laser Array Intensity | 4.8 W/cm$^2$ |

As the operation of the polarization chamber 14 has been described in detail, overall system operation will now be described. FIG. 6 shows a flow diagram generally at 200 indicating the operation of the system shown in FIG. 1. At step 202, the alkali metal is input into the polarization chamber 14 as needed. At step 204, the temperature control chamber 16 senses whether or not the polarization chamber temperature is correct in order to optimize the pressure and density of the alkali metal vapor. If the chamber temperature is not correct, the temperature control chamber, through its control circuitry, adjusts the chamber temperature as shown in step 206. At step 208, the input valve 20 is opened and a predetermined quantity of the xenon/buffer gas mixture flows through the tubing 18 into the polarization chamber. At step 210, the laser diode array 22 optically pumps the alkali metal vapor to induce a spin polarization in the alkali metal vapor. Although steps 204–210 are shown to occur in the above order, it should be understood that the steps may be interchanged without affecting overall system operation.

At step 212, the optically pumped alkali metal vapor polarizes the $^{129}$Xe gas through atomic collisions between the alkali metal vapor atoms and the $^{129}$Xe gas atoms. At step 214, after the $^{129}$Xe gas is polarized, the gaseous mixture within the polarization chamber expands out into the separator 24 through the tubing 26. The separator then removes the alkali metal vapor from the now polarized $^{129}$Xe/buffer gas mixture before the gas mixture flows through output valve 28 to the system/user interface 32. The polarized gas is then used in a specific application as indicated at step 216. At step 218, if the application is over, the process ends. If the application is not over, the process returns to step 202 and repeats itself. Thus, it should be understood that the system of the present invention may be operated in either a continuous or a batch mode.

As described above, the present invention is directed to a method and apparatus for producing polarized $^{129}$Xe gas in an efficient and cost effective manner. The system of the present invention is compact and portable, therefore allowing the system to be implemented in a clinical setting. Further, the system of the present invention is relatively easy to operate and trouble shoot, and is relatively inexpensive to maintain, therefore making the production of polarized $^{129}$Xe gas possible from a commercial standpoint.

While the above description constitutes the preferred embodiment of the present invention, it should be appreciated that the invention may be modified without departing from the proper scope or fair meaning of the accompanying claims. Various other advantages of the present invention will become apparent to those skilled in the art after having the benefit of studying the foregoing text and drawings taken in conjunction with the following claims.

In the claims:

1. A system for producing polarized xenon-129 gas, comprising:

a storage tank containing a quantity of non-polarized xenon-129 gas;

a polarization chamber for controllably receiving a quantity of said non-polarized xenon-129 gas from said storage tank, said polarization chamber containing a predetermined quantity of alkali metal having an associated alkali metal vapor;

a tunable broadband light source positioned relative to said polarization chamber for optically pumping said alkali metal vapor, said optically pumped metal vapor causing collisional polarization of said xenon-129 gas; and means for separating said alkali metal vapor from said polarized xenon-129 gas subsequent to said polarization of said xenon-129 gas.

2. The system of claim 1, further comprising temperature controlling means for said polarization chamber for regulating temeprature, and therefore density, of said alkali metal vapor for optimizing collisional polarization of said non-polarized xenon-129 gas.

3. The system of claim 1, wherein said tunable broadband light source is a diode laser array.

4. The system of claim 1, wherein said alkali metal is rubidium.

5. The system of claim 1, wherein said polarization chamber is located in a magnetic field having a strength and spatial homogeneity sufficient for magnetic gradient induced depolarization of the xenon-129 atoms to be insignificant.

6. The system of claim 5, further comprising a magnetic resonance imaging machine for producing said magnetic field wherein said light from said tunable broadband light source is projected along a direction of the magnetic field and through the polarization chamber, said light being resonant with an alkali atomic transition that induces an electron spin polarization in said alkali metal vapor collinear to the magnetic field via said optical pumping.

7. The system of claim 1, wherein said non-polarized xenon gas includes a buffer gas to broaden a rubidium absorption line to increase efficiency of said broadband light source.

8. The system of claim 7, wherein said buffer gas is nitrogen.

9. The system of claim 1, further comprising an input valve wherein said non-polarized xenon-129 gas is controllably input into said polarization chamber through said input valve.

10. A method of producing polarized xenon-129 gas, comprising the steps of:

providing a polarization chamber;

introducing a quantity of an alkali metal into said chamber, said alkali metal having an associated alkali metal vapor;

controlling the temperature of said polarization chamber to maintain said alkali metal vapor density at a predetermined level;

optically pumping said alkali metal vapor with a tunable broadband light source to polarize said alkali metal vapor atoms;

introducing a predetermined quantity of non-polarized xenon gas into said chamber containing said alkali metal, said non-polarized xenon-129 gas including a buffer gas;

transferring polarization of said alkali metal vapor atoms to said non-polarized xenon-129 atoms; and causing said gaseous mixture in said polarization chamber to expand into means for separating said alkali metal vapor atoms from said polarized xenon-129 atoms.

11. The method of claim 10, further comprising the step of projecting light from said light source used for optically pumping said alkali metal vapor in a direction along a magnetic field generated by a magnetic resonance imaging machine.

12. A method of delivering a quantity of polarized xenon-129 gas, comprising the steps of:

providing a polarization chamber;

introducing a quantity of an alkali metal into said chamber, said alkali metal having an associated alkali metal vapor;

controlling the temperature of said polarization chamber to maintain said alkali metal vapor density at a predetermined level;

optically pumping said alkali metal vapor with a tunable broadband light source to polarize said alkali metal vapor atoms;

introducing a predetermined quantity of non-polarized xenon-129 gas into said chamber containing said alkali metal, said non-polarized xenon-129 gas including a buffer gas;

transferring polarization of said alkali metal vapor atoms to said non-polarized xenon-129 atoms;

supplying said separated, polarized xenon-129 gas to a system/patient interface;

separating the polarized xenon-129 gas from the alkali metal vapor; and causing said polarized xenon-129 gas to be ingested by a patient through said interface for magnetic resonance imaging.

* * * * *

UNITED STATES PATENT AND TRADEMARK OFFICE
CERTIFICATE OF CORRECTION

PATENT NO. : 5,617,860
DATED : April 8, 1997
INVENTOR(S) : Timothy Chupp, Kevin P. Coulter, Eduardo Oteiza, Ronald Walsworth It is certified that error appears in the above-indentified patent and that said Letters Patent is hereby corrected as shown below:

Column 1 of the cover page, under [56] References Cited
WO-95 27438 PCT Publication is not cited
(submitted by Applicants on October 9, 1996 and
entered by Examiner on March 18, 1997)

Column 2, line 67, "$_3$He" should be --$^3$He--

Column 10, line 43, Claim 2, "temeprature" should be --temperature--

Signed and Sealed this

Second Day of December, 1997

Attest:

Attesting Officer

BRUCE LEHMAN

Commissioner of Patents and Trademarks